(12) United States Patent
Klegraf et al.

(10) Patent No.: US 9,523,106 B2
(45) Date of Patent: Dec. 20, 2016

(54) PROCESS FOR THE ENZYMATIC PRODUCTION OF CARNITINE FROM BETA-LACTONES

(75) Inventors: Ellen Klegraf, Brig-Glis (CH); Manuela Avi, Kufstein (AT)

(73) Assignee: LONZA LTD., Visp (CH)

( * ) Notice: Subject to any disclaimer, the term of this patent is extended or adjusted under 35 U.S.C. 154(b) by 212 days.

(21) Appl. No.: 13/557,922

(22) Filed: Jul. 25, 2012

(65) Prior Publication Data
US 2013/0034885 A1   Feb. 7, 2013

Related U.S. Application Data

(60) Provisional application No. 61/512,032, filed on Jul. 27, 2011.

(30) Foreign Application Priority Data

Jul. 27, 2011   (EP) .................................... 11006163

(51) Int. Cl.
| | | |
|---|---|---|
| C12P 13/00 | (2006.01) | |
| C12P 7/42 | (2006.01) | |
| C12P 7/62 | (2006.01) | |
| C12P 41/00 | (2006.01) | |

(52) U.S. Cl.
CPC ............... *C12P 13/007* (2013.01); *C12P 7/42* (2013.01); *C12P 7/62* (2013.01); *C12P 41/005* (2013.01)

(58) Field of Classification Search
CPC .............. C12P 7/42; C12P 7/62; C12P 41/005
USPC ........................................ 435/135, 128, 146
See application file for complete search history.

(56) References Cited

U.S. PATENT DOCUMENTS

| | | |
|---|---|---|
| 5,473,104 A | 12/1995 | McCarthy |
| 2006/0046286 A1 | 3/2006 | Watanabe et al. |
| 2007/0213524 A1 | 9/2007 | Coates et al. |
| 2008/0311633 A1 | 12/2008 | Habicher et al. |

FOREIGN PATENT DOCUMENTS

| | | |
|---|---|---|
| CH | 680588 A5 | 9/1992 |
| WO | WO2009/062731 A1 | 5/2009 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
Pencreach et al, Enz & Micro Tech 2001, 28, pp. 473-479.*
Torres et al Food Tech Biotech 2004, 42 pp. 271-277.*
Yang,et al., "Cloning, expression and characterization of a novel thermal stable and short-chain alcohol tolerant lipase from Burkholderia cepacia strain G63", J. Mol., Catal., B Enzymatic 45, 2007, pp. 91-96.
Scott G. Nelson, et al., "Sequential Acyl Halide—Aldehyde Cyclocondensation and Enzymatic Resolution as a Route to Enantiomerically Enriched B-Lactones", J. Org. Chem., 2000, 65, 1227-1230.
Jose A. Lopez-Lopez, et al., "Synthesis of chlorinated B- and y-lactones from unsaturated acids with sodium hypochlorite and Lewis acids", Tetrahedron Letters 48, 2007, 1749-1752.
Zhen Qian, et al., "Structural redesign of Lipase B from Candida antarctica by Circular Permutation and Incremental Truncation" J. Mol. Biol. (2009), 393, pp. 191-201.
Sophie Peuch-Guenot, et al., "Small-scale Production of Burkholderia cepacia ATCC21808 Lipase Adapted to High-Throughput", J. Biomol. Screen., 2008, 13(1), pp. 72-79.
S. Jorgensen, et al., "Cloning, Sequence, and expression of a lipase gene from Pseudomonas cepacia: lipase production in heterologous hosts requires two Pseudomonas genes", J. Bacteriol. 1991, 173, pp. 559-567.
Sohel Dalal, et al. "Purification and Properties of the alkaline lipase from Burkholderia cepacia A.T.C.C. 25609", J. Biotechnol. Appl. Biochem. 2008, 51, pp. 23-31.
UniProt identifier P41365[26-342].
UniProt Identifier P220888[45-364].
European Search Report dated Jan. 9, 2012 issued in European Patent Application No. EP 11006163.
Song, et al., "New Method for the Preparation of (R)-Carnitine", Tetrahedron: Asymmetry vol. 6, No. 5, p. 1063-1066, 1995.
Lee, et al., "Method for Preparing optically active alkyl 3-hydroxybutanoate derivative", XP 002666098, Database Caplus, Chemical Abstracts Service, 2009.

* cited by examiner

*Primary Examiner* — Robert Mondesi
*Assistant Examiner* — MD. Younus Meah
(74) *Attorney, Agent, or Firm* — Hoffmann & Baron, LLP

(57) ABSTRACT

Subject of the invention is a process for the production of L-carnitine, wherein a β-lactone, which is a 4-(halomethyl) oxetane-2-one, is converted into L-carnitine, wherein the process comprises an enzymatic conversion of the β-lactone into (R)-4-halo-3-hydroxybutyric acid or (R)-4-halo-3-hydroxybutyric acid ester.

13 Claims, No Drawings

SEQUENCE LISTING

```
<160> NUMBER OF SEQ ID NOS: 2

<210> SEQ ID NO 1
<211> LENGTH: 320
<212> TYPE: PRT
<213> ORGANISM: Burkholderia cepacia
<220> FEATURE:
<221> NAME/KEY: SOURCE
<222> LOCATION: 1..320
<223> OTHER INFORMATION: /mol_type="protein"
      /note="Mature Protein"
      /organism="Burkholderia cepacia"

<400> SEQUENCE: 1
```

Ala Ala Gly Tyr Ala Ala Thr Arg Tyr Pro Ile Ile Leu Val His Gly
1               5                   10                  15

Leu Ser Gly Thr Asp Lys Tyr Ala Gly Val Leu Glu Tyr Trp Tyr Gly
                20                  25                  30

Ile Gln Glu Asp Leu Gln Gln Asn Gly Ala Thr Val Tyr Val Ala Asn
            35                  40                  45

Leu Ser Gly Phe Gln Ser Asp Asp Gly Pro Asn Gly Arg Gly Glu Gln
    50                  55                  60

Leu Leu Ala Tyr Val Lys Thr Val Leu Ala Ala Thr Gly Ala Thr Lys
65                  70                  75                  80

Val Asn Leu Val Gly His Ser Gln Gly Gly Leu Ser Ser Arg Tyr Val
                85                  90                  95

Ala Ala Val Ala Pro Asp Leu Val Ala Ser Val Thr Thr Ile Gly Thr
            100                 105                 110

Pro His Arg Gly Ser Glu Phe Ala Asp Phe Val Gln Asp Val Leu Ala
        115                 120                 125

Tyr Asp Pro Thr Gly Leu Ser Ser Val Ile Ala Ala Phe Val Asn
    130                 135                 140

Val Phe Gly Ile Leu Thr Ser Ser Ser His Asn Thr Asn Gln Asp Ala
145                 150                 155                 160

Leu Ala Ala Leu Gln Thr Leu Thr Thr Ala Arg Ala Ala Thr Tyr Asn
                165                 170                 175

Gln Asn Tyr Pro Ser Ala Gly Leu Gly Ala Pro Gly Ser Cys Gln Thr
            180                 185                 190

Gly Ala Pro Thr Glu Thr Val Gly Gly Asn Thr His Leu Leu Tyr Ser
        195                 200                 205

```
Trp Ala Gly Thr Ala Ile Gln Pro Thr Leu Ser Val Phe Gly Val Thr
    210                 215                 220

Gly Ala Thr Asp Thr Ser Thr Leu Pro Leu Val Asp Pro Ala Asn Val
225                 230                 235                 240

Leu Asp Leu Ser Thr Leu Ala Leu Phe Gly Thr Gly Thr Val Met Ile
                245                 250                 255

Asn Arg Gly Ser Gly Gln Asn Asp Gly Leu Val Ser Lys Cys Ser Ala
                260                 265                 270

Leu Tyr Gly Lys Val Leu Ser Thr Ser Tyr Lys Trp Asn His Leu Asp
                275                 280                 285

Glu Ile Asn Gln Leu Leu Gly Val Arg Gly Ala Tyr Ala Glu Asp Pro
290                 295                 300

Val Ala Val Ile Arg Thr His Ala Asn Arg Leu Lys Leu Ala Gly Val
305                 310                 315                 320

<210> SEQ ID NO 2
<211> LENGTH: 317
<212> TYPE: PRT
<213> ORGANISM: Candida antarctica
<220> FEATURE:
<221> NAME/KEY: SOURCE
<222> LOCATION: 1..317
<223> OTHER INFORMATION: /mol_type="protein"
     /note="Mature Protein"
     /organism="Candida antarctica"

<400> SEQUENCE: 2

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
                100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
        130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
                180                 185                 190

Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225                 230                 235                 240
```

-continued

```
Leu Arg Ser Thr Thr Gly Gln Ala Arg Ser Ala Asp Tyr Gly Ile Thr
            245             250             255

Asp Cys Asn Pro Leu Pro Ala Asn Asp Leu Thr Pro Glu Gln Lys Val
            260             265             270

Ala Ala Ala Ala Leu Leu Ala Pro Ala Ala Ala Ala Ile Val Ala Gly
            275             280             285

Pro Lys Gln Asn Cys Glu Pro Asp Leu Met Pro Tyr Ala Arg Pro Phe
            290             295             300

Ala Val Gly Lys Arg Thr Cys Ser Gly Ile Val Thr Pro
305             310             315
```

PROCESS FOR THE ENZYMATIC PRODUCTION OF CARNITINE FROM BETA-LACTONES

CROSS-REFERENCE TO RELATED APPLICATIONS

This application claims the benefit of priority from European Patent Application No. 11006163.7 filed Jul. 27, 2011 and U.S. Provisional Patent Application No. 61/512,032 filed Jul. 27, 2011, the disclosures of which are incorporated herein by reference.

INCORPORATION OF SEQUENCE LISTING

Incorporated herein in its entirety and submitted herewith is the computer readable Sequence Listing for the above-identified Application. The Sequence Listing is disclosed on a computer-readable ASCII text file titled "SequenceListing1686-444.txt", date modified on Jul. 24, 2012. The sequence.txt file is 5.74 KB size.

BACKGROUND OF THE INVENTION

The invention relates to methods for the production of L-carnitine.

Carnitine (vitamin Bt; 3-hydroxy-4-trimethylammoniobutanoate) is a quaternary ammonium compound biosynthesized from the amino acids lysine and methionine. In living cells, it is required for the transport of fatty acids from the cytosol into the mitochondria during the breakdown of lipids for the generation of metabolic energy. It is used as a nutritional supplement. Carnitine exists in two stereoisomers. The biologically active form is L-carnitine, whilst its enantiomer, D-carnitine, is biologically inactive. When producing L-carnitine in an industrial process, it is desirable to produce the biologically active L-form in high purity.

Various methods were described for the industrial production of L-carnitine. Microbiological processes are known, in which L-carnitine is produced directly by bacteria. In other processes, a racemate is produced by organic synthesis and separated subsequently into enantiomers.

Further, attempts have been made to synthesize L-carnitine directly from chiral precursors. A group of potential precursors are chiral cyclic lactones. Since methods for obtaining chiral lactones are known in principle, L-carnitine is available upon hydrolysis of the lactone ring.

U.S. Pat. No. 5,473,104 discloses a process for the preparation of L-carnitine from (S)-3-hydroxybutyrolactone. The process is a two-step process, wherein in a first step (S)-3-hydroxybutyrolactone is converted into the corresponding hydroxy-activated lactone, whilst maintaining the ring structure. In a second step, the ring of the activated lactone is opened and the trimethylammonium group is introduced with trimethylamine. Altogether, the reaction is relatively complicated because it requires the activation of an intermediate with harsh chemicals.

CH 680 588 A5 discloses a process for producing L-carnitine from a β-lactone precursor, wherein a chiral 2-oxetanone is converted into L-carnitine in a two-step process. In a first step, 4-(chloromethyl)-2-oxetanone is subjected to a hydrolysis step, in which the ring is opened and 4-chloro-3-hydroxybutyric acid is obtained. In a subsequent step, the acid is converted into L-carnitine with trimethylamine. However, the production of chiral β-lactones requires relatively complicated heavy metal catalysts and the yields are often not sufficient.

Nelson & Spencer (J. Org. Chem. 2000, 65, 1227-1230) disclose a process for obtaining enantiomerically enriched β-lactones from β-lactone racemates by enzymatic resolution with lipases. The substrates used are various alkyl- and aryl-β-lactone racemates. As summarized in Table 1, the yields are only sufficient for a limited number of reactions. The enantioselectivity depends strongly on the substituents of the β-lactone and the enantiomeric yield for the small substituent methyl is very low (table 1). The reactions require organic solvents, such as benzyl alcohol, which is not desirable for industrial applications for environmental reasons. The reaction times are relatively long (mostly 72 hours).

US 2006/0046286 discloses methods for obtaining chiral β-butyrolactones and 3-hydroxycarboxylic acid esters by enzymatic esterification from β-lactones. As for Nelson & Spencer, the use of lipases is suggested. The reactions require organic solvents, such as toluene, and relatively long reaction times for about 16 hours. The substrate is β-butyrolactone. In most experiments, the substrate is not a racemate, but optically active (R)-β-butyrolactone. The specific reactions mostly yield (R)-β-butyrolactone at enhanced enantiomeric purity, whereas (S)-3-hydroxybutyric acid esters, if at all, are obtained only in relatively low amounts (examples 1, 6, 7).

Since enantiomerically pure L-carnitine is an important industrial product, it would be desirable to provide further efficient processes for its production. Specifically, it would be desirable to provide processes for the production of L-carnitine in a relatively simple manner at a high total yield and enantiomeric yield.

Problem Underlying the Invention

The problem underlying the invention is to provide a method for producing L-carnitine, which overcomes the above-mentioned drawbacks. Specifically, the problem is to provide an efficient and simple process for the production of L-carnitine.

The total yield as well as the chiral yield shall be high. The number of process steps shall be relatively low and the process shall not require complicated apparatuses. Overall, the process shall have a high be atom economy and shall be cost and labour efficient. The chemicals used shall be readily available and should not be too expensive.

It is a further problem underlying the invention to provide a mild process, which avoids harsh conditions and harsh chemicals. Chemicals, which affect the environment, such as organic solvents or heavy metals, or those which could affect the health of the workers, such as aromatic solvents, should be avoided. Heavy metal catalysts, which have to be removed, but nonetheless may remain as trace impurities in the product, shall be avoided. Specifically, no expensive catalysts comprising precious metals, such as platinum, should be used. The overall energy input shall be low. Specifically, the reaction should be carried out at relatively low temperatures and for relatively low reaction times.

DISCLOSURE OF THE INVENTION

Surprisingly, the problem underlying the invention is solved by the process according to the claims. Further inventive embodiments are disclosed throughout the description.

Subject of the invention is a process for the production of L-carnitine, wherein a β-lactone, which is a 4-(halomethyl) oxetane-2-one, is converted into L-carnitine, wherein the process comprises an enzymatic conversion of the β-lactone into (R)-4-halo-3-hydroxybutyric acid or (R)-4-halo-3-hydroxybutyric acid ester.

The carnitine is L-carnitine ((R)-carnitine, levocarnitine). L-carnitine is the physiologically active stereoisomer of carnitine. The reaction product of the enzymatic conversion is an (R)-4-halo-3-hydroxybutyric acid or an ester thereof, depending on whether the enzymatic conversion is carried out in aqueous medium or in alcohol. This intermediate product can be converted into L-carnitine in a subsequent reaction step. The configuration of the chiral carbon of the acid or ester is (R), as for the corresponding L-carnitine. Thus, the subsequent conversion into L-carnitine can be carried out simply by replacing the halogen atom of the intermediate by a trimethylammonium group by means of a nucleophilic substitution, whilst the chirality remains unaffected.

In specific embodiments of the invention, the β-lactone is 4-(chloromethyl)oxetane-2-one, 4-(bromomethyl)oxetane-2-one or 4-(iodomethyl)oxetane-2-one. The use of 4-(chloromethyl)oxetane-2-one is preferred.

Preferably, the enzyme is stereoselective for the (R)-isomer of the β-lactone. In other words, preferably the enzyme converts exclusively, or at least predominantly, the (R)-lactone into the corresponding (R)-acid or acid ester. Thus, when the substrate is a β-lactone racemate, or at least comprises (S)-β-lactone and (R)-lactone, the enzyme selectively converts the (R)-β-lactone into the corresponding (R)-acid or acid ester, whereas the (S)-β-lactone remains unaffected or essentially unaffected. Thus the corresponding (S)-β-lactone remains and accumulates in the reaction mixture. Thus, the (R)-acid or acid ester is enriched in the product. Further, the (S)-β-lactone will be enriched in the product. Both compounds can be separated from each other due to their different solubilities in water and organic solvent. When starting from a β-lactone racemate, an ideal enzymatic reaction would yield a mixture of 50% Mol-% (R)-acid or acid ester (with an optical purity of 100% ee) and 50 Mol-% of residual (S)-β-lactone, which subsequently would be removed from the mixture.

In a preferred embodiment of the invention, the β-lactone is a racemate. Preferably, an enantiomeric excess of the (R)-4-halo-3-hydroxybutyric acid or (R)-4-halo-3-hydroxybutyric acid ester is obtained. The enantiomeric excess (in relation to (S)-4-halo-3-hydroxybutyric acid or ester) is preferably higher than 80%, more preferably higher than 90%, 95% or 99% ee.

The enzymatic conversion is carried out in the presence of a solvent. Preferably, the solvent comprises water. Water may be present in a one-phase system or a two-phase system. In the presence of water, a (R)-4-halo-3-hydroxybutyric acid is obtained. The enzymatic conversion is then an enzymatic hydrolysis. As a result of the enzymatic hydrolysis, (R)-4-chloro-3-hydroxybutyric acid, (R)-4-bromo-3-hydroxybutyric acid or (R)-4-iodo-3-hydroxybutyric acid is obtained.

Preferably, the solvent is exclusively water. When using water as a solvent, the initial reaction mixture is a solution or suspension. In this embodiment, the reaction mixture is preferably a one-phase system, in which a clear phase separation between an aqueous phase and a liquid organic phase is not observed.

In another preferred embodiment of the invention, the enzymatic conversion is carried out in a two phase system, wherein (R)-4-halo-3-hydroxybutyric acid is enriched in the aqueous phase. In a two-phase system, the relatively non-polar β-lactone substrate is enriched in the organic phase, whereas the ionic acid product is enriched in the aqueous phase. Thus after finishing the reaction, the phases can be separated and the aqueous phase already comprises a relatively pure product. The organic phase may comprise any solvent, in which the β-lactone is highly soluble and the acid is poorly soluble. In comparison, the one-phase system in aqueous medium requires less organic solvent overall and is thus advantageous for economic and environmental reasons.

Examples of the solvent include hydrocarbons, such as aliphatic hydrocarbons such as pentane, hexane, heptane, octane, decane and cyclohexane, aromatic hydrocarbons such as toluene and xylene; halogenated hydrocarbons such as dichloromethane, 1,2-dichloroethane, chloroform, carbontetrachloride and o-dichlorobenzene; ethers such as diethyl ether, diisopropyl ether, tert-butyl methyl ether, dimethoxyethane, ethylene glycol diethyl ether, tetrahydrofuran, 1,4-dioxane and 1,3-dioxolane; amides such as formamide; sulfoxides such as dimethyl sulfoxide.

In another embodiment of the invention, the solvent is an alcohol, preferably an alcohol comprising 1 to 5 carbon atoms, more preferably methanol, ethanol or propanol. When carrying out the enzymatic conversion in an alcohol and in the absence of water, the product is a linear ester. Subsequently, when the ester is converted into L-carnitine, it is de-esterified.

In a preferred embodiment of the invention, after enzymatic conversion, residual β-lactone is removed from the solution. Preferably, the residual β-lactone is removed by extraction with a solvent. For example, when the solution is carried out in a one-phase system, the residual β-lactone may be extracted with an ester, such as ethylacetate, or with hexane. Preferably, multiple extractions with relatively low amounts of solvent are carried out.

In a preferred embodiment, the enzyme is a hydrolase (Enzyme Commission number EC 3). Hydrolases yields two products from a substrate by hydrolysis. Preferably, the hydrolase is an esterase (EC 3.1) or a peptidase (EC 3.4). An esterase is a hydrolase enzyme, such as a lipase, that hydrolyses esters into an acid and an alcohol. A peptidase (protease) is an enzyme that conducts proteolysis, that is, hydrolysis of a peptide bond.

In a preferred embodiment of the invention, the enzyme is a lipase. The lipase is selective for the (R)-β-lactone. Preferably, the lipase is from fungi, yeasts or bacteria. This means that the organism was the origin of the lipase. However, the lipase may be an artificial, especially a recombinant, lipase. Such lipases are commercially available, for example from the companies Novozymes, Amano Enzyme or Nagase.

Preferably, the enzyme is a triacylglycerol lipase. Such lipases of enzyme class 3.1.1.3 catalyze hydrolysis of triglycerides into fatty acids and glycerols.

Lipases from fungi, yeasts or bacteria are often synthesized in vivo as inactive precursors. These precursors are processed and secreted. Such lipases are typically extracellular lipases. Mature proteins are generated by cleaving off N-terminal peptides, such as signal peptides or propeptides. According to the invention, the lipase is preferably a mature lipase. In other words, it is preferably in the active form. The inventive process is preferably an in vitro process.

The lipase may comprise a catalytic triad of amino acids Ser-His-Asp. For example, such lipases are found in yeast, such as *Candida*.

In preferred embodiments of the invention, the lipase is from *Candida, Pseudomonas, Aspergillus, Bacillus* or *Ther-*

*momyces*. The lipase may be a derivative of such a lipase, preferably one having at least 75%, preferably at least 90%, sequence identity.

Preferably, the lipase is from *Candida, Pseudomonas* or *Aspergillus*. More preferably, the lipase is from *Pseudomonas cepacia* (*Burkholderia cepacia*), *Pseudomonas fluorescens* or *Candida antarctica*. The lipase may be a derivative of such a lipase, preferably one having at least 75%, preferably at least 90%, sequence identity.

Derivatives are obtainable by amino acid substitution, deletion, insertion or modification. Preferably, derivatives are obtained by recombinant DNA modification methods. Such recombinant lipases may have higher stabilities and efficiencies compared to their natural precursors.

Especially preferred are lipases from *Pseudomonas cepacia* and/or lipase B from *Candida antarctica*. It was found that these enzymes provide the desired products at high total and enantiomeric yield.

In a highly preferred embodiment, the enzyme is lipase from *Pseudomonas cepacia* of SEQ ID NO:1 (UniProt identifier P22088[45-364]; Joergensen et al., J. Bacteriol. 1991; 173, p559-567). The mature protein is a protein having 320 amino acids. It is derived from a 364 amino acid precursor comprising a signal peptide and a propeptide.

In another preferred embodiment, the enzyme is lipase from *Pseudomonas cepacia* having an amino acid sequence different from SEQ ID NO:1. *P. cepacia* comprises several lipases with amino acid sequences of high homology with SEQ ID NO:1. For example, the enzyme may be *P. cepacia* alkaline lipase (NCBI Acc. No: ABX71757.1; Dalal et al., J. Biotechnol. Appl. Biochem. 2008; 51, p23-31). This alkaline lipase has about 98% sequence identity with the lipase of SEQ ID NO:1. The enzyme may also be *P. cepacia* lipase (Genbank: ABN09945.1; Yang et al., J. Mol. Catal., B Enzym. 2007; 45, p91-96). This lipase has about 92% sequence identity with lipase of SEQ ID NO:1.

Lipase B from *Candida antarctica* of SEQ ID NO:2 (UniProt identifier P41365[26-342]) is a protein having 317 amino acids. The mature protein is derived from a 342 amino acid precursor comprising a signal peptide and a propeptide.

Preferably, the derivative is a derivative of lipase from *Pseudomonas cepacia* of SEQ ID NO:1 and/or from lipase B from *Candida antarctica* of SEQ ID NO:2, preferably one having at least 75%, preferably at least 90%, sequence identity compared to SEQ ID NO:1 and/or SEQ ID NO:2. As used herein, sequence identity is preferably determined by BLAST according to standard parameters. Derivatives of such lipases obtainable by amino acid substitution, deletion, insertion or modification, and methods for obtaining such derivatives, are known in the art. For example, derivatives of lipase B from *Pseudomonas cepacia* having increased catalytic activity and methods for their production are disclosed in Puech-Guenot et al., J. Biomol. Screen. 2008; 13(1), p72-79. Derivatives of lipase B from *Candida antarctica* having increased catalytic activity and methods for their production are disclosed in Qian et al., J. Mol. Biol. 2009; 393; p191-201.

In a preferred embodiment of the invention, the enzymatic conversion is carried out at a temperature between 0° C. and 50° C., preferably between 20° C. and 40° C., specifically about 25° C. or about 30° C. The temperature is adjusted in view of the specific enzyme used.

In a preferred embodiment of the invention, the enzymatic conversion is carried out in aqueous solution comprising 0.1 to 50 weight % β-lactone, more preferably between 0.1 and 10 weight % or between 0.5 and 3 weight % β-lactone.

The reaction is carried out in an appropriate buffer. The buffer is adapted to the specific enzyme used. Mostly, the pH will be approximately neutral, for example between 5 and 9, or between 7 and 8. If necessary, the pH may be adapted during the reaction to remain stable by the addition of a base or an acid.

In a preferred embodiment, the reaction mixture consists of the buffer, enzyme and β-lactone. Additives might be added, for example those which enhance the stability or the turnover of the enzyme, such as salts, metal ions or cofactors. Overall, the reaction requires only a low number of chemicals and can be carried out in a relatively simple manner at mild temperatures.

When a desired amount of the acid or acid ester is obtained, the reaction is terminated. The reaction may be terminated by removing the enzyme, for example by filtration. When using a β-lactone racemate as a substrate and a highly selective enzyme, up to 50% of the β-lactone may be converted into the corresponding (R)-acid or (R)-acid ester. After removal and isolation, residual (S)-β-lactone may be used for other reactions.

The reaction time may be between 1 to 50 hours, preferably between 2 to 20 hours. It was found that with some enzymes an efficient turnover can be achieved within 10 hours, specifically within 8 hours.

Mono-halogenated β-lactones for carrying out the inventive ring opening reaction are known in the art. In view of the stereoselectivity of the enzyme, a β-lactone racemate can be used in the inventive process. Mono-halogenated β-lactones are obtainable e.g. by low pressure carbonylation of the corresponding epoxides as disclosed in US2007/0213524 A1 or starting from unsaturated acid using Lewis acid and hypochlorite as described by Lopez-Lopez, Jose; Tetrahedron Letters 2007, 48(10), 1749-1752.

In a preferred embodiment of the invention, chiral 4-(halomethyl)oxetane-2-ones are obtained by a [2+2] cycloaddition reaction in the presence of a catalyst. In a specific embodiment of the invention, a chiral β-lactone is used. This may enhance the enantiomeric yield in the inventive reaction. A chiral β-lactone can be obtained by a [2+2] cycloaddition of ketene with an aldehyde X—$CH_2$—CHO, wherein X is selected from Cl, Br and I, in the presence of a chiral catalyst. Ketene (ethenone, formula $C_2H_2O$) is a colorless gas, which is highly reactive due to two adjacent double bonds in the molecule.

In a preferred embodiment of the invention, the 4-halo-3-hydroxybutyric acid or (R)-4-halo-3-hydroxybutyric acid ester obtained in the enzymatic conversion is subsequently converted into L-carnitine with trimethylamine (TMA). Preferably, the halogen atom is substituted by a trimethylamine group in a nucleophilic substitution reaction. The TMA can be brought into contact with the β-lactone in the presence of a base. The base might be added after bringing the β-lactone in contact with the TMA.

In a preferred embodiment of the inventive process, the β-lactone is converted into L-carnitine in a two-step process. In a first step, a 4-(chloromethyl)-2-oxetanone is subjected to the enzymatic hydrolysis, in which the β-lactone ring is opened and 4-chloro-3-hydroxybutyric acid is obtained. In a subsequent step, the acid, ester is converted into L-carnitine with trimethylamine.

An exemplified inventive process for the synthesis of L-carnitine is shown in scheme 1 below. The process comprises a [2+2] cycloaddition of ketene and an aldehyde of the formula Cl—$CH_2$—CHO. The resulting β-lactone racemate 1 is subjected to the enzymatic ring cleavage reaction to yield the corresponding (R)-acid 2a (in water as a solvent)

or (R)-ester 2b (in alcohol). The acid 2a or ester 2b is then converted into L-carnitine with TMA.

Scheme 1: Synthesis of L-carnitine

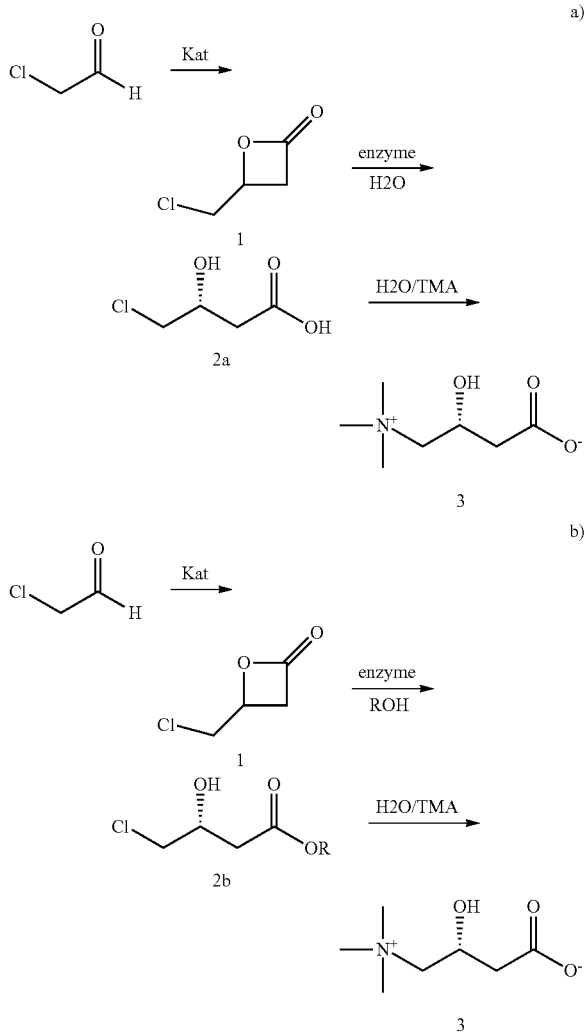

In a preferred embodiment of the invention, the TMA is recycled during the process. Since TMA is available in gaseous form, it can be led through the reaction fluid, collected and recycled. In the reaction medium, dissolved TMA can be separated from the mixture after reaction is finished (e.g by distillation) and reintroduced in the process. Preferably, the TMA is reintroduced into the reaction pathway in a cyclic process. TMA is commercially available in the form of a pure gas (Fluka Chemicals) or in the form of an aqueous solution of 10 to 40 wt. %. The amount of TMA in the reaction mixture may be between 1 and 3 equivalents, preferably between 1 and 2.5 equivalents. However, the amount and excess of TMA is less critical than the amount of metal hydroxide, because it can be recycled during the reaction and reintroduced into the reaction chamber.

Another subject of the invention is a process for the production of a (R)-4-halo-3-hydroxybutyric acid or (R)-4-halo-3-hydroxybutyric acid ester, wherein the process comprises an enzymatic conversion of a β-lactone, which is a 4-(halomethyl)oxetane-2-one, into (R)-4-halo-3-hydroxybutyric acid or (R)-4-halo-3-hydroxybutyric acid ester. These reaction products are valuable intermediates for the production of L-carnitine. They may be converted into L-carnitine in a simple nucleophilic substitution, wherein the chirality remains unaffected. In addition, they might be used for the synthesis of other organic compounds or derivatives of L-carnitine.

In a preferred embodiment of the invention, in the enzymatic conversion the total yield of (R)-4-halo-3-hydroxybutyric acid or (R)-4-halo-3-hydroxybutyric acid ester is between 40% and 50%, based on the total initial amount of β-lactone, and/or the enantiomeric purity of the (R)-4-halo-3-hydroxybutyric acid or (R)-4-halo-3-hydroxybutyric acid ester is at least 90%, more preferably at least 95%.

The inventive process solves the problems underlying the invention. The process is relatively simple and economical and requires only a low number of process steps. Thus side reactions are avoided and the total yield and enantiomeric yield are high. Since the enzymatic conversion may use enzymatic resolution, it is possible to start from a β-lactone racemate. Thus, it is not necessary to use expensive chiral reactants.

The reaction conditions are mild, because neither harsh chemicals, such as heavy metal catalysts, nor high amounts of organic solvents are necessary. The process requires relatively low amounts of energy for heating. In principle, only enzymes are necessary as additives, which can be removed easily and are generally non-hazardous. The intermediate is thus especially applicable for producing the food additive L-carnitine.

EXAMPLES

An enzymatic resolution was carried out in a one-phase aqueous system. The substrate was a 4-(chloromethyl)oxetane-2-one racemate, which was converted into a mixture of (R)-4-chloro-3-hydroxybutyric acid and residual (S)-β-lactone as illustrated by scheme 2 below.

Scheme 2: Enzymatic resolution of a β-lactone racemate according to the examples.

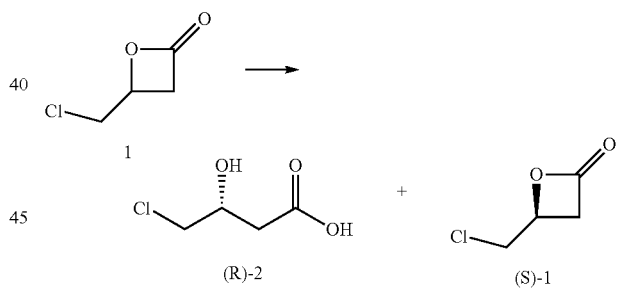

Analytics

The reaction is monitored by gas chromatography (GC) on a Lipodex E column. 4-(Chloromethyl)-2-oxetanone 1 is analyzed by GC on a Lipodex E column. 4-Chloro-3-hydroxybutyric acid 2 is derivatized using a chiral, fluorescent reagent. The reaction mixture is analyzed by HPLC using an ODS-column and flourimetric detection.

Example 1

To a solution or suspension of 12.5 mg enzyme in 5.0 mL potassium phosphate buffer (0.1 M, pH 7.5), 50 mg 4-(chloromethyl)-2-oxetanone 1 is added and the reaction mixture is stirred at 30° C. The pH is continually adjusted to 7.5 with 0.5 M KOH. At regular intervals, 200 µL samples are taken, extracted with 400 µL ethyl acetate, filtered and analyzed by chiral GC. After complete hydrolysis of the (R)-enantiomer, the enzyme is centrifuged off and the reaction mixture is extracted twice with 5.0 mL ethyl acetate. (R)-4-chloro-3- hydroxy butyric acid 2 is obtained as aqueous solution. 5 Reactions were carried out with different lipases as summarized in table 1 below. Conversion and enantiomeric purities are shown in table 1. (S)-1 and (R)-2 are both obtained at high enantiomeric purity. The reaction time at 30° C. was only between 4 to 8 hours.

TABLE 1

Summary of conditions and results of examples 1 to 5.

| Ex. | Enzyme, Source | Commercial Name, Supplier | Reaction Time [h] | Convers. [%] | ee [%] (S)-1 | ee [%] (R)-2 |
|---|---|---|---|---|---|---|
| 1 | lipase Pseudomonas cepacia | Lipase PS-C Amano | 6 | 52 | 99.9 | 99.7 |
| 2 | lipase Pseudomonas cepacia | Lipase PS Amano | 4 | 44 | 99.9 | 96.0 |
| 3 | lipase Pseudomonas fluorescens | Lipomod L056P | 6 | 55 | 99.9 | 91.5 |
| 4 | lipase B Candida antarctica | Novozyme 435 | 7.5 | 48 | 99.9 | 99.8 |
| 5 | Lipase | Lipase P Nagase | 8 | 41 | 99.9 | 85.0 |

The invention claimed is:

1. A process for the production of L-carnitine, wherein a β-lactone, which is a 4-(halomethyl)oxetane-2-one, is converted into L-carnitine, wherein the process comprises enzymatic conversion of the β-lactone into (R)-4-halo-3-hydroxybutyric acid, wherein the enzymatic conversion is carried out with a lipase in an aqueous medium, the lipase having the amino acid sequence of SEQ ID NO: 1 or SEQ ID NO: 2, wherein the enantiomeric purity of the (R)-4-halo-3-hydroxybutyric acid is at least 95% e.e., and conversion of (R)-4-halo-3-hydroxybutyric acid into L-carnitine with trimetylamine.

2. The process of claim 1, wherein the β-lactone is a racemate.

3. The process of claim 2, wherein an enantiomeric excess of the (R)-4-halo-3-hydroxybutyric acid is obtained.

4. The process of claim 1, wherein the enzymatic conversion is carried out in a two phase solution, wherein (R)-4-halo-3-hydroxybutyric acid is enriched in the aqueous phase.

5. The process of claim 1, wherein after enzymatic conversion, residual β-lactone is removed from the solution.

6. The process of claim 5, wherein the residual β-lactone is removed by extraction with a solvent.

7. The process of claim 1, wherein the lipase is from *Candida, Pseudomonas, Aspergillus, Bacillus* or *Thermomyces*.

8. The process of claim 1, wherein the lipase is from *Pseudomonas cepacia, Pseudomonas fluorescens*, or *Candida antarctica*.

9. The process of claim 1, wherein the enzymatic conversion is carried out at a temperature between 0° C. and 50° C., and/or wherein the enzymatic conversion is carried out in an aqueous solution comprising 0.1 to 10 weight % β-lactone.

10. The process of claim 9, wherein the enzymatic conversion is carried out at a temperature between 20° C. and 40° C., and/or wherein the enzymatic conversion is carried out in aqueous solution comprising 0.1 to 10 weight % β-lactone.

11. The process of claim 1, in which the β-lactone is synthesized in a preceding step in a [2+2] cycloaddition of ketene and an aldehyde of the formula X-CH2-CHO, wherein x is selected from Cl, Br and I.

12. The process of claim 1, wherein the total yield of (R)-4-halo-3-hydroxybutyric acid in the enzymatic conversion is between 40% and 50%, based on the total initial amount of β-lactone.

13. The process of claim 1, wherein the reaction time of the enzymatic conversion of the β-lactone into (R)-4-halo-3-hydroxybutyric acid is less than 10 hours.

* * * * *